(12) United States Patent
Ananthan (10) Patent No.: US 8,129,406 B2
(45) Date of Patent: Mar. 6, 2012

(54) NONPEPTIDE INHIBITORS OF MATRIX METALLOPROTEINASES

(75) Inventor: Subramaniam Ananthan, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 775 days.

(21) Appl. No.: 10/593,748

(22) PCT Filed: Mar. 21, 2005

(86) PCT No.: PCT/US2005/009263
§ 371 (c)(1), (2), (4) Date: Jul. 28, 2008

(87) PCT Pub. No.: WO2005/092844
PCT Pub. Date: Oct. 6, 2005

(65) Prior Publication Data
US 2008/0312329 A1 Dec. 18, 2008

Related U.S. Application Data

(60) Provisional application No. 60/555,380, filed on Mar. 22, 2004.

(51) Int. Cl.
*A61K 31/445* (2006.01)
*A61K 31/41* (2006.01)
*C07D 211/06* (2006.01)
*C07D 257/06* (2006.01)

(52) U.S. Cl. ........ 514/315; 546/184; 546/248; 548/250; 548/253; 514/381

(58) Field of Classification Search .................. 546/184, 546/248; 548/250, 252, 253; 514/315, 381
See application file for complete search history.

(56) References Cited

U.S. PATENT DOCUMENTS

| | | | | |
|---|---|---|---|---|
| 5,753,653 | A | 5/1998 | Bender et al. ............... | 514/227.5 |
| 5,977,408 | A | 11/1999 | Levin et al. .................... | 562/622 |
| 6,326,516 | B1 * | 12/2001 | Levin et al. .................... | 562/622 |
| 6,642,255 | B2 * | 11/2003 | Xue et al. ...................... | 514/312 |

FOREIGN PATENT DOCUMENTS

| | | |
|---|---|---|
| EP | 818442 | 1/1998 |
| EP | 780386 | 10/2002 |
| WO | WO 98/16506 | 10/1997 |
| WO | WO 97/44315 | 11/1997 |
| WO | WO 98/47494 | 10/1998 |
| WO | WO 00/44711 A | 8/2000 |
| WO | WO 00/63165 | 10/2000 |
| WO | WO 02/055491 | 9/2002 |

OTHER PUBLICATIONS

Xue et al (2002): STN International HCAPLUS database, (Columbus, Ohio), Accession No. 2002:539654.*

Apfel et al., "Hydroxaminc acid derivatives as potent peptide deformylase inhibitors and antibacterial agents," *J. Med. Chem.*, 43:2324-2331 (2000).
Armarego et al., "Quinazolines. Part XIII. Synthesis and stereochemistry of trans- and cis-decahydroquinazolines," *J. Chem. Soc.* (C), 1635-1641 (1969).
Auerbach et al., "Assays for angiogenesis: A review," *Pharm. Ther.*, 51:1-11 (1991).
Bailey et al., "Reduction of cyclic anhydrides with NaBH$_4$, versatile lactone synthesis," *J. Org. Chem.*, 35:3574-3576 (1970).
Beckett et al., "Recent advances in matrix metalloproteinase inhibitor research," *Drug Disc. Today*, 1:16-26 (1996).
Bernath et al., "Preparation and conformational study of partially saturated 3,1-benzoxazines,3,1-benzoxazin-2-ones and 3,1-benzoxazine-2-thiones," *Tetrahedron*, 41:1353-1365 (1985).
Birkedal-Hansen et al., "Matrix metalloproteinase: A review," *Crit. Rev. Oral. Biol. Med.*, 4:197-250 (1993).
Bode et al., "The x-ray crystal structure of the catalytic domain of human neutrophil collagenase," *EMBO J.*, 13:1263-1269 (1994).
Brown, "MMP inhibitors in the treatment of cancer," *Med. Oncology*, 14:1-10 (1997).
Brown, "Clinical studies with MMP inhibitors," *APMIS*, 107:174-180 (1999).
Brown, "Ongoing trials with matrix metalloproteinase inhibitors," *Expert Opin. Invest. Drugs*, 9:2167-2177 (2000).
Burns et al., "Nanomolar inhibitors for two distinct biological target families for a single synthetic sequence: A next step in combinatorial library design?"*Angew. Chem. Int. Ed.*, 37:2848-2850 (1998).
Caldwell et al., "Phosphinic acid inhibitors of matrix metalloproteinases," *Bioorg. Med. Chem. Lett.*, 6:323-328 (1996).
Cheng et al., "Design and synthesis of piperazine-based MMP inhibitors," *J. Med. Chem.*, 43:369-380 (2000).
Clark et al., "Computational methods for the prediction of drug-likeness," *Drug Discov. Today*, 5:49-58 (2000).
Cockett et al., "MMPs and metastatic cancer," *Biochem. Soc. Symp.*, 63:295-313 (1998).
Curren et al., "MMPs—their role in tumor invasion and metastasis," *Eur. J. Cancer*, 36:1621-1630 (2000).
Davidson et al., "The Inhibition of Matrix Metalloproteinase Enzymes," *Chem. Ind.*, 258-261 (1997).

(Continued)

*Primary Examiner* — Golam M M Shameem
(74) *Attorney, Agent, or Firm* — Ballard Spahr LLP (57) ABSTRACT

Disclosed are selective inhibitors of matrix metalloproteinases represented by the following formula (I).

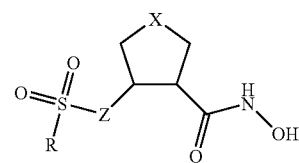

(I)

wherein X is $(CH_2)_nO$, $(CH_2)_nS$, $(CH_2)_nNR^1$, $(CH_2)_n(CH_2)$, or CH=CH, wherein n=0, 1, or 2; R and $R^1$ are, independently, a substituted or unsubstituted alkyl, alkenyl, alkynyl, aryl, heteroaryl group, cycloalkyl, heterocycloalkyl, cycloalkenyl, or heterocycloalkenyl; and Z is NH or $CH_2$; or a pharmaceutically acceptable salt thereof. Also disclosed are methods of making such compounds and methods of using such compounds to inhibit tumor progression and to treat diseases such as arthritis.

14 Claims, 1 Drawing Sheet

OTHER PUBLICATIONS

De et al., "The next generation of MMP inhibitors: Design and synthesis," *Ann NY Acad Sci* 878:40-60 (1999).
Eddershaw et al., "ADME/PK—app to drug discovery," *Drug Disc. Today*, 5:409-414 (2000).
Finzel et al., "Structural characterizations of nonpeptidic thiadiazole inhibitors of matrix metalloproteinases reveal the basis for stromelysin selectivity," *Protein Sci.*, 7:2118-2126 (1998).
Freskos et al., "Discovery of a novel series of selective MMP inhibitors: Identification of the γ-sulfone-thiols," *Bioorg. Med. Chem. Lett.*, 9:943-948 (1999).
Galazka et al., "Spontaneous propeptide processing of ministromelysin-1 mutants blocked my APMA," *Biochem.*, 38:1316-1322 (1999).
Gatto et al., "BAY 12-9566, a novel inhibitor of MMPs with angiogenic activity," *Clin. Cancer Res.*, 5:3603-3607 (1999).
Gavuzzo et al., "Two crystal structures of human collagenase with primed and unprimed-side inhibitor," *J. Med. Chem.*, 43:3377-3385 (2000).
Getman et al., "Discovery of a novel class of potent HIV-1 protease inhibitors," *J. Med. Chem.* 36:288-291 (1993).
Goodly et al., "In vivo modulation of human tumor cell growth by normal human extracellular matrix," *Tumor Biology*, 15:326-336 (1994).
Gopurala et al., "A novel synthetic peptide inhibits tumor invasion and angiogenesis in human cell-biomatrix models," *Proc. Am. Assoc. Cancer. Res.*, 39:44, Abstract #301 (1998).
Gowravaram et al., "Inhibition of MMPs by hydroxamates containing heteroatom-based modifications of the P1 group," *J. Med. Chem.*, 38:2570-2581 (1995).
Harmat et. al., "1,2-disustituted cyclohexane derived tripeptide adlehydes as novel selective thromin inhibitors," *Bioorg. Med. Chem. Lett.*, 8:1249-1254 (1998).
Heath et al., "Clinical potential of MMP inhibitors in cancer therapy," *Drugs*, 59:1043-1055 (2000).
Hidalgo et al., "Biotech company shares dive after drug failure," *BJM*, 321:1039 (2000).
Hidalgo et al., "Development of MMP inhibitors in cancer therapy," *JNCI*, 93:178-193 (2001).
Ikeda et al., "Inhibition of gelatinolytic activity in tumor tissues by MMP inhibitors-Application of film in situ zymography," *Clin. Cancer. Res.*, 6:3290-3296 (2000).
Keiner et al., "MMP and metastatis," *Can. Chemo. Pharm.*, 43:42-51 (1999).
Kennewell et al., "Sythesis of γ-aminobutyric acid analogues of restricted conformation-2-(aminometh)cycloalkanecarboxyllic acids," *J. Chem. Soc. Perkin. Trans. I*, 2563-2570 (1982).
Kiyama et al., "Homology modeling of gelatinase catalytic domains and docketing simulations of novel sulfonamide inhibitors," *J. Med. Chem.*, 42:1723-1738 (1999).
Kleinfeld et al., "X-ray absorption studies of human MMP-2 bound to a selective mechanismbased inhibitor," *JBC*, 276:17125-17131 (2001).
Kleinman et al., Basement membrane complexes with biological activity, *Biochem.*, 25:312-318 (1986).
Krumme et al., "Hydroxamate derivatives of substrate-analogous peptides containing aminomalonic acid are potent inhibitors of matrix metalloproteinases," *FEBS Lett.*, 436:209-212 (1998).
Kruger et al., "Hydroxamate-type MMP inhibitor Batimastat promotes liver matastasis," *Cancer Res.*, 61:1272-1275 (2001).
Kurokawa et al., "Synthesis of Octahydro-11-oxodibenz[b,e]oxepins and -Octahydro-11-oxodibenz[b,e]thiepins," *Chem. Pharm. Bull.* 31:4312-4318 (1983).
Levin et al., "The synthesis and biological activity of a novel series of diazepine MMP inhibitors," *Bioorg. Med. Chem. Lett.*, 8:2657-2662 (1998).
Levin et al., "Heteroaryl and cycloalkyl sulfonamide hydroxamic acid inhibitors of matrix metalloproteinases," *Med. Chem. Lett.*, 11:239-242 (2001).
Levy et al, "MMP inhibitors: A structure-activity study," *J. Med. Chem.*, 41:199-223 (1998).
Lovejoy et al., "Crystal structure of MMP-1 and -13 reveal the structural basis for selectivity of callaginase complexed with an inhibitor," *Science*, 263:375-377 (1994).
MacDougall et al., "MMP: multifunctional contributors in tumor progression," *Cancer Metastasis Rev.*, 14:351-362 (1995).
MacPherson et al., "Discovery of CGS 27023A, a non-peptidic, potent, and orally active stromelysin inhibitor that blocks cartilage degradation in rabbits," *J. Med. Chem.*, 40:2525-2532 (1997).
Maki et al., "Augmented anti-metastasis efficacy of a selective matrix metalloproteinase inhibitor, MMI-66, in combination with CPT-11," *Clin. Exp. Metastasis*, 19:519-526 (2002).
Matter et al., "Quantitative structure—activity relationship of human neutrophil collagenase (MMP-8) inhibitors using comparative molecular field analysis and X-ray structure analysis," *J. Med. Chem.*, 42:1908-1920 (1999).
Matter et al., "Affinity and selectivity of MMP inhibitors. A chemometric study," *J. Med. Chem.*, 42:4506-4523 (1999).
McCawley et al., "MMP: multifunctional contributors in tumor progression," *Mol. Med. Today*, 64:149-156 (2000).
Michaelides et al., "Recent advances in MMP inhibitors in cancer therapy," *Curr. Pharma. Design*, 5:787-819 (1999).
Morgunova et al., "Structure of human pro-matrix metalloproteinase-2: Activation mechanism revealed," *Science*, 284:1667-1670 (1999).
Moriconi and Mazzocchi, "Synthesis of cis- and trans-7-azabicyclo[4.2.0]octanes," *J. Org. Chem.*, 31:1372-1379 (1996).
Newman et al., "The conversion of phenols to thiophenols via dialkythiocarbamates," *J. Org. Chem.*, 31:3980-3984 (1960).
Ngu et al., "A new efficient solid phase synthesis of hydroxamic acids," *J. Org. Chem.*, 62:7088-7089 (1997).
Node et al., "Hard acid and soft nucleuphile systems-5. ring-opening reaction of lactones to ω-alkylthio or ω-arylthio carboxylic acids with aluminum halide and thiol.," *J. Org. Chem.*, 46:5163-5166 (1981).
O'Brien et al., "Structure-activity relationship and pharmacokinetic analysis for a series of potent, systemically available biphenylsulfona MMP inhibitors," *J. Med. Chem.*, 43:156-166 (2000).
Ohta et al., "Effect of combination therapy with matrix metalloproteinase inhibitor MMI-166 and mitomycin C on the growth and liver metastasis of human colon cancer," *Japanese J. Cancer. Res.*, 92:688-695 (2001).
Pavlovsky et al., "X-ray structure of human stromelysin catalytic domain complexed with nonpeptide inhibitors: Implications for inhibitor selectivity," *Protein Sci.*, 8:1455-1462 (1999).
Ratnikov et al., "Determination of MMP activity using biotinylated gelatin," *Anal. Biochem.*, 286:149-155 (2000).
Reiter et al., "Inhibition of MMP-1 and MMP-13 with phosphinic acids that exploit binding in the $S_2$ pocket," *Bioorg. Med. Chem. Lett.*, 9:127-132 (1999).
Rich, In *Comprehensive Medicinal Chemistry*; Hansch, C.; Sammes, P.; Taylor, J.B., Eds.; Pergamon Press: New York, 2:391-441 (1990).
Russo, "MMP may provide clues in multiple aliments," *Scientist*, Jul. 5, 1999.
Santos et al., "Rodent pharmacokinetic and anti-tumor efficacy studies with a series of synthetic inhibitors of matrix metalloproteinases," *Clin. Exp. Metastasis.*, 15:499-508 (1997).
Seymour, "Novel anticancer agents in development: Exciting prospects and new challenges," *Cancer Treat. Rev.*, 25:301-312 (1999).
Shalinski et al., "Broad antitumor and antiangiogenic activities of AG3340, a potent and selective MMP inhibitor undergoing advanced oncology clinical trials," *Ann. NY Acad. Sci.*, 878:236-270 (1999).
Siegal et al., "In vitro inhibition of human sarcoma cells' invasive ability of BABIM—a novel human extracellular matrix," *Tumor Biology*, 15:326-336 (1994).
Siegal et al., "Development of a human reconstituted biomatrix for qunatitation of the invasiveness," *Cancer Lett.*, 69:123-132 (1993).
Singh et al., "Relationship between structure and bioavailability in a series of hydroxamate based MMI," *Bioorg. Med. Chem. Lett.*, 5:337-342 (1995).
Skiles et al., "MMP inhibitors for treatment of cancer," *Ann. Rep. Med. Chem.*, 35:167-176 (2000).
Skotnicki et al., "Design and synthetic considerations of MMI," *Ann. NY Acad. Sci*, 878:61-72 (1999).
SBIR Grant#R43CA71285-01 Feb. 27, 1997.

Spurlino, "Structual implications in the design of matrix-metalloproteinase inhibitors." In Structure-Based Drug Design, Veerapandian, Ed., Marcel Dekker, Inc., N.Y., 171-189 (1997).

Stams et al., "Structure of human neutrophil collagenase reveals large S1' specificity pocket," *Nature: Struct. Biol.*, 1:119-123 (1994).

Stetler-Stevenson et al., "Type IV collagenases in tumor invasion and metastasis," *Cancer Metastasis Rev.*, 9:289-303 (1990).

Sticht et al., "Solution structure of the glycosylated second type 2 module of fibronectin," *J. Mol. Biol.*, 276:177-187 (1998).

Stockman et al., "Solution structure of SL complexed to thiadiazole inhibitors," *Protein Sci.*, 7:2281-2286 & 2281-2286 (1998).

Summers et al., "Matrix metalloproteinase inhibitors and cancer," *Ann. Rep. Med. Chem.*, 33:131-140 (1998).

Tamura et al., "Highly selective and orally active inhibitors of type IV collagenase (MMP-9 and MMP-2): N-sulfonylamino acid derivatives," *J. Med. Chem.*, 41:640-649 (1998).

Turbanti et al., "1,2-Cyclomethylenecarboxylic monoamide hydroxamic derivatives. A novel class on non-aminoacid ACE inhibitors," *J. Med. Chem.*, 36:699-707 (1993).

Vu et al., "MMP-9/gelatinase-B," In "MMPs" Park W. & Mecham R., AP, NY, p. 115-149 (1998).

Vukicevik et al., "Identification of multiple growth factors in Matrigel suggest caution in interpretation of cellular activity," *Exp. Cell Res.*, 202:1-8 (1992).

Windsor et al., "Catalytic domain comparisons of human fibroblast-type collagenase, stromelysin-1 and matrilysin," *BBA*, 1334:261-272 (1999).

Williams et al., "Renin inhibitors containing conformationally restricted P1-P2 dipeptides," *J. Med. Chem.*, 34:887-900 (1991).

Woessner, "MMP family," In "MMP" Park W. & Mecham R., AP, NY, p. 1-14 (1998).

Woessner, "MMP inhibition: From the Jurassic to the third millennium," *Ann. NY Aca. Sci.*, 878:388-403 (1999).

Yu et al., "MMP-2/gelatinase-A," In "MMPs" Park W. & Mecham R., AP, NY, p. 85-113 (1998).

International Search Report and Written Opinion for PCT/US05/009263.

International Preliminary Report on Patentability for PCT/US05/009263.

\* cited by examiner

Fig. 1

NONPEPTIDE INHIBITORS OF MATRIX METALLOPROTEINASES

CROSS REFERENCE TO RELATED APPLICATION

This application claims benefit of priority to U.S. Provisional Application 60/555,380, filed Mar. 22, 2004. U.S. Provisional Application 60/555,380 is hereby incorporated by reference herein in its entirety.

BACKGROUND

Matrix metalloproteinases ("MMPs") are a class of zinc-dependent endopeptidase enzymes involved in the degradation and repair of major components of extracellular matrix and connective tissue. MMPs can be found in various cell types that reside in or are associated with connective tissues, such as fibroblasts, monocytes, macrophages, endothelial cells, and also invasive or metastatic tumor cells. MMPs are secreted from cells as latent proenzymes and are activated by Zn-dependent cleavage of the N-terminal part of the protein. When active MMPs are stimulated by growth factors and cytokines in the local tissue environment, they can degrade protein components of extracellular matrix and connective tissue, such as collagen, proteoglycans, fibronectin, and laminin. See H. Birkedal-Hansen, *Crit. Rev. Oral. Biol. Med.,* 1993, 4, 197-250.

Currently, it is known that there are fourteen different MMPs. These enzymes can be classified into several major categories according to their substrate specificities. For example, MMP-1, MMP-8, and MMP-13 are classified as collagenases. MMP-3 and MMP-11 are classified as stromelysins. MMP-2 and MMP-9 are classified as Type IV collagenases/gelatinases.

MMPs are of significant interest because they have been implicated in a wide variety of physiological and pathological conditions. Some examples of conditions known to be mediated by MMPs are tumor growth, osteoarthritis, rheumatoid arthritis, septic arthritis, restenosis, fibrosis, MMP-mediated osteopenias, inflammatory diseases of the central nervous system, reproduction, tissue morphogenesis, angiogenesis, skin aging, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, periodontal disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection. See M. Cockett, et al., *Biochem. Soc. Symp.,* 1998, 63, 295-313; D. Keiner, et al., *Can. Chemo. Pharm.,* 1999, 43, 42-51; D. Keiner, *Cancer Metastasis Rev.,* 1990, 9, 289-303; J. MacDougall, et al., *Mol. Med. Today,* 2000, 64, 149-156; J. MacDougall, et al., *Cancer Metastasis Rev.,* 1995, 14, 351-362; S. Curren, et al., *Eur. J. Cancer,* 2000, 36, 1621-1630.

One particular area of research that has received much attention is the involvement of MMPs with cancer and the growth and spread of tumors. Indeed, the metastatic spread of cancer via proteolytic degradation of host biomatrix poses one of the greatest challenges in the treatment of cancer. Considerable evidence has been accumulated that indicates the involvement of MMPs in general, and of the gelatinases in particular, in local tumor growth, invasion, and metastatic spread of cancer to disseminated sites. For example, the level of expression of MMP-2 and MMP-9 is known to be elevated in certain tumor progression events. These enzymes degrade Type IV collagen, the major component of basement membranes, and denatured collagen (gelatin), leading to tumor metastasis. Also, the disruption of vascular membranes, composed mainly of Type IV collagen, by MMP-2 and MMP-9 is known to play a critical role in tumor metastasis.

Because of the involvement MMPs have in such a wide variety of physiological and pathological conditions, especially cancer and arthritis, synthetic inhibitors of these enzymes are considered attractive targets in drug discovery research. See J. B. Summers, et al., *Ann. Rep. Med. Chem.,* 1998, 33, 131-140; A. H. Davidson, et al., *Chem. Ind.,* 1997, 258-261; J. C. Spurlino, In "Structure-Based Drug Design," Veerapandian, Ed., Marcel Dekker, Inc., N.Y., 1997, 171-189; R. P. Beckett, et al., *Drug Disc. Today,* 1996, 1, 16-26. Such research pursuits have resulted in the development of several broad-spectrum peptidyl and partially selective nonpeptidyl MMP inhibitors as potential anticancer and antiarthritis agents. See P. D. Brown, *Med. Oncology,* 1997, 14, 1-10; P. D. Brown, *APMIS,* 1999, 107, 174-180; P. D. Brown, *Expert Opin. Invest. Drugs,* 2000, 9, 2167-2177; J. Freskos, et al., *Biorg. Med. Chem. Lett.,* 1999, 9, 943-948; L. J. MacPherson, et al., *J. Med. Chem.,* 1997, 40, 2525-2532; M. Cheng, et al., *J. Med. Chem.,* 2000, 43, 369-380. However, current results from both preclinical and clinical trials of MMP inhibitors have been disappointing mainly due to poor bioavailability, poor selectivity, and undesirable side effects, such as tissue toxicity and even the promotion of liver metastasis. See "MMPs," Park W & Mecham R., AP, NY, 1998, pp. 1-14, 85-113, 115-149; M. Michaelides, et al., *Curr. Pharma. Design,* 1999, 5, 787-819; E. Heath, et al., *Drugs,* 2000, 59, 1043-1055; L. Seymour, *Cancer Treat. Rev.,* 1999, 25, 301-312; K. Woessner, *Ann. NY Aca. Sci.,* 1999, 878, 388-403; J. Skiles, et al., *Ann. Rep. Med. Chem.,* 2000, 35, 167-176; M. Gowravaram, et al., *J. Med. Chem.,* 1995, 38, 2570-2581; M. Gowravaram, et al., *Biorg. Med. Chem. Lett.,* 1995, 5, 337-342; R. Greenwald, et al., *Curr. Opin. Ther. Patents,* 1995, 4, 7-16; D. Levy, et al., *J. Med. Chem.,* 1998, 41, 199-223; A. Kruger, et al., *Cancer Res.,* 2001, 61, 1272-1275. Therefore, in light of the clinical complexity associated with current MMP inhibitors, there is currently a need for new, potent inhibitors that more selectively target MMPs.

SUMMARY

In accordance with the purposes of the disclosed materials, compositions, and methods, as embodied and broadly described herein, in one aspect, the disclosed subject matter relates to a compound having the following formula:

wherein X is $(CH_2)_nO$, $(CH_2)_nS$, $(CH_2)_nNR^1$, $(CH_2)_n(CH_2)$, or $CH=CH$, wherein $n=0$, 1, or 2; R and $R^1$ are, independently, a substituted or unsubstituted alkyl, alkenyl, alkynyl, aryl, heteroaryl group, cycloalkyl, heterocycloalkyl, cycloalkenyl, or heterocycloalkenyl; and Z is NH or $CH_2$; or a pharmaceutically acceptable salt thereof.

In another aspect, the disclosed subject matter relates to a method for using the compounds described herein by administering an amount effective for modulation of matrix metalloprotease of at least one compound described herein to an environment comprising the matrix metalloprotease.

In yet another aspect, the disclosed subject matter relates to a method for using the compounds described herein by administering an amount effective for modulation of tumor metastasis of at least one compound described herein to a cell.

In a further aspect, the disclosed subject matter relates to a method for treating a subject with cancer comprising administering an effective amount of a compound described herein to a subject in need of the treatment.

In a still further aspect, the disclosed subject matter relates to a method for preventing cancer in a subject comprising administering an effective amount of a compound described herein to a subject.

In another aspect, the disclosed subject matter relates to a method for treating a subject with arthritis comprising administering an effective amount of a compound described herein to a subject in need of the treatment.

In still another aspect, the disclosed subject matter relates to selective modulators of matrix metalloproteinases and selective inhibitors of metalloproteinases. Also described herein are modulators of cancer metastasis and diseases such as arthritis. Further, methods of making and using such compounds are disclosed.

Additional advantages will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

The disclosed materials, compounds, compositions, and methods may be understood more readily by reference to the following detailed description of specific aspects of the materials and methods and the Examples included therein and to the Figure and the previous and following description.

Before the present materials, compounds, compositions, and/or methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Disclosed are materials, compounds, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound having a given formula is disclosed and discussed and a number of modifications that can be made to a number of R groups in the formula are discussed, each and every combination and permutation of the compound and the modifications to the R groups that are possible are specifically contemplated unless specifically indicated to the contrary. Thus, if a class of substituents A, B, and C are disclosed as well as a class of substituents D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

DEFINITIONS

In this specification and in the claims which follow, reference will be made to a number of terms which shall be defined to have the following meanings:

As used in the specification and the appended claims, the singular forms "a," "an" and "the" include plural referents unless the context clearly dictates otherwise. Thus, for example, reference to "a compound" includes mixtures of compounds; reference to "an aryl substituent" includes mixtures of two or more such aryl substituents, and the like.

"Optional" or "optionally" means that the subsequently described event or circumstance may or may not occur, and that the description includes instances where the event or circumstance occurs and instances where it does not. For example, the phrase "optionally substituted aryl group" means that the aryl group may or may not be substituted and that the description includes both unsubstituted aryl groups and aryl groups where there is substitution.

Ranges may be expressed herein as from "about" one particular value and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "activity" as used herein refers to a biological activity. The term "pharmacological activity" as used herein refers to the inherent physical and/or chemical properties of a compound, molecule, modulator, or inhibitor. These properties include but are not limited to efficacy, half-life, solubility, stability, affinity, and other pharmacokinetic and pharmacodynamic properties.

The terms "peptide" and "peptidyl" as used herein respectively refer to a class of compounds and chemical moieties composed of amino acids chemically bound together. In general, the amino acids are chemically bound together via amide linkages (CONH). "Peptide" and "peptidyl" as used herein include oligomers of amino acids and small and large peptides, including polypeptides and proteins. The terms "nonpeptide" or "nonpeptidyl" refer to a class of compounds that are not composed of amino acids chemically bound together via an amide linkage.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol, as described below. The term "halogenated alkyl" specifically refers to an alkyl group that is substituted with one or more halide, e.g., fluorine, chlorine, bromine, or iodine.

The term "alkoxy" as used herein is an alkyl group bound through a single, terminal ether linkage; that is, an "alkoxy" group may be defined as —OA where A is alkyl as defined above.

The term "alkenyl" as used herein is a hydrocarbon group of from 2 to 24 carbon atoms with a structural formula containing at least one carbon-carbon double bond. Asymmetric structures such as (AB)C=C(CD) are intended to include both the E and Z isomers. This may be presumed in structural formulae herein wherein an asymmetric alkene is present, or it may be explicitly indicated by the bond symbol C=C.

The term "alkynyl" as used herein is a hydrocarbon group of 2 to 24 carbon atoms with a structural formula containing at least one carbon-carbon triple bond.

The term "aryl" as used herein is any carbon-based aromatic group including, but not limited to, benzene, naphthalene, phenyl, biphenyl, phenoxybenzene, etc. The term "aromatic" also includes "heteroaryl," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and contains at least one carbon-carbon double bound, C=C. Examples of cycloalkenyl groups include, but are not limited to, cyclopropenyl, cyclobutenyl, cyclopentenyl, cyclopentadienyl, cyclohexenyl, etc. The term "heterocycloalkenyl" is a cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein.

The term "aldehyde" as used herein is represented by the formula —C(O)H.

The terms "amine" or "amino" as used herein are represented by the formula $NAA^1A^2$, where A, $A^1$, and $A^2$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH.

The term "ester" as used herein is represented by the formula —OC(O)A or —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $AOA^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $AC(O)A^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxamate" as used herein is represented by the formula C(O)NHOH.

The term "hydroxyl" as used herein is represented by the formula —OH.

The term "nitro" as used herein is represented by the formula —$NO_2$.

The term "silyl" as used herein is represented by the formula —$SiAA^1A^2$, where A, $A^1$, and $A^2$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfo-oxo" as used herein is represented by the formulas —S(O)A, —S(O)$_2$A, —OS(O)$_2$A, or —OS(O)$_2$OA, where A can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$A, where A can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "sulfone" as used herein is represented by the formula $AS(O)_2A^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "sulfoxide" as used herein is represented by the formula $AS(O)A^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

"X," "Y," "R," "$R^1$," and "$R^2$" as used herein can, independently, possess one or more of the groups listed above. For example, if R is a straight chain alkyl group, one of the hydrogen atoms of the alkyl group can optionally be substituted with a hydroxyl group, an alkoxy group, etc. Depending upon the groups that are selected, a first group can be incorporated within second group or, alternatively, the first group can be pendant (i.e., attached) to the second group. For example, with the phrase "an alkyl group comprising a sulfonyl group," the sulfonyl group can be incorporated within the backbone of the alkyl group. Alternatively, the sulfonyl group can be attached to the backbone of the alkyl group. The nature of the group(s) that is (are) selected will determine if the first group is embedded or attached to the second group.

As used herein, by a "subject" is meant an individual. Thus, the "subject" can include mammals (e.g., primate, human, etc.), domesticated animals (e.g., cats, dogs, etc.), livestock (e.g., cattle, horses, pigs, sheep, goats, etc.), laboratory animals (e.g., mouse, rabbit, rat, guinea pig, etc.), and birds. In one aspect, "subject" is a mammal. In another aspect, "subject" is a human.

Reference to a "cell" herein can include a cell in vitro. Alternatively, reference to a "cell" can include a cell in vivo, which can be found in a subject. A "cell" can be a cell from any organism including, but not limited to, a bacterium, a eukaryote, or an animal.

By the term "effective amount" of a compound as provided herein is meant a nontoxic but sufficient amount of a compound to provide the desired result, e.g., modulation or inhibition. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation. Similarly, by the phrase "amount effective for modulation of a MMP" is meant a nontoxic but sufficient amount of a compound to modulate the activity of at least one MMP. Also, by the phrase "amount effective for inhibition of a MMP" is meant a nontoxic but sufficient amount of a compound to inhibit the activity of at least one MMP. Again, the exact amount will vary from subject to subject, depending on the species, age, and general condition of the subject, the severity of the disease that is being treated, the particular compound used, its mode of administration, and the like.

The phrase "environment comprising the MMP" is meant any environment where one or more MMP is present. Such environments can include, but are not limited to, subjects, organs, tumors, cells, gels, solutions, or neat MMP.

By "pharmaceutically acceptable" is meant a material that is not biologically or otherwise undesirable, i.e., the material can be administered to an individual along with the selected compound without causing any undesirable biological effects or interacting in a deleterious manner with any of the other components of the pharmaceutical composition in which it is contained.

Reference will now be made in detail to specific aspects of the disclosed materials, compounds, compositions, components, and methods, examples of which are illustrated in the accompanying drawing.

Compounds

In one aspect, described herein are compounds having Formula I:

wherein X is (CH$_2$)$_n$O, (CH$_2$)$_n$S, (CH$_2$)$_n$NR$^1$, (CH$_2$)$_n$(CH$_2$), or CH=CH, wherein n=0, 1, or 2; R and $R^1$ are, independently, a substituted or unsubstituted alkyl, alkenyl, alkynyl, aryl, heteroaryl group, cycloalkyl, heterocycloalkyl, cycloalkenyl, or heterocycloalkenyl; and Z is NH or $CH_2$; or a pharmaceutically acceptable salt thereof.

In another aspect, described herein are compounds having Formula I, wherein Z is NH, R is a substituted or unsubstituted aryl or heteroaryl group; X is $(CH_2)_nO$, $(CH_2)_nS$, $(CH_2)_nNR^1$, $(CH_2)_n(CH_2)$, or CH=CH, wherein n=0, 1, or 2, and wherein $R^1$ is a substituted or unsubstituted alkyl, alkenyl, alkynyl, aryl, heteroaryl group, cycloalkyl, heterocycloallcyl, cycloalkenyl, or heterocycloalkenyl; or a pharmaceutically acceptable salt thereof.

In one aspect, described herein are compositions comprising a compound represented by Formula I.

The labels α and β are included in Formula I, as well as in other structures used herein, as aids to help identify and distinguish the particular carbon atom positions for further discussion. The choice of these labels is merely arbitrary and is not intended to be a limitation.

In the compounds represented by Formula I the pharmacophores, e.g. the substituent that contains the sulfonyl group and the substituent that contains the hydroxamate group, are attached to adjacent carbon atoms, i.e., carbons α and β. Also, the two carbon framework carrying the pharmacophores, i.e., carbons α and β, is conformationally constrained by cyclic substitution. Further, in the pharmacophore containing the sulfonyl group, the sulfonyl group is positioned in the γ-position to the hydroxamate group, i.e., there are three atoms in between the sulfonyl group and the hydroxamate group.

Compounds represented by Formula I can be optically active or racemic. The stereochemistry at carbons α and β can vary and will depend upon the spatial relationship between the substituent that contains the sulfonyl group and the hydroxamate group to one another. In one aspect, the stereochemistry at carbon α is S. In another aspect, the stereochemistry at carbon α is R. In one aspect, the stereochemistry at carbon β is S. In another aspect, the stereochemistry at carbon β is R. Using techniques known in the art, it is possible to vary the stereochemistry at carbons α and β.

Unless stated to the contrary, a formula with chemical bonds shown only as solid lines and not as wedges or dashed lines contemplates each possible isomer, e.g., each enantiomer and diastereomer, and a mixture of isomers, such as a racemic mixture.

Also described herein are the pharmaceutically acceptable salts of compounds represented by Formula I. Pharmaceutically acceptable salts are prepared by treating the hydroxamate and/or the sulfonamide with an appropriate amount of a pharmaceutically acceptable base. Representative pharmaceutically acceptable bases include ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C., such as at room temperature. The molar ratio of compounds represented by Formula I to be used is chosen to provide the ratio desired for any particular salts. For preparing, for example, the ammonium salts of the hydroxamate, the hydroxamate can be treated with approximately one equivalent of pharmaceutically acceptable base to yield a neutral salt.

In one aspect, the R group in Formula I can be a substituted aryl group that is represented by the following formula.

wherein $R^2$ is Br; methoxy;

wherein Y=O, S, or $CH_2$;

In another aspect, the R group in Formula I can be p-methoxyphenyl, p-biphenyl, p-phenoxyphenyl, p-(phenylethynyl)phenyl, p-(phenylethenyl)phenyl, and linear tricyclic systems with three aryl groups or two aryl groups tethered to a central piperidinyl ring system and their heteroaromatic analogues.

A non-exhaustive list of specific examples of compounds that are represented by Formula I are shown below.

1 cis
2 trans

-continued 3 cis
4 trans

5 cis
6 trans

7 cis
8 trans a: $R^2$ = Br
b: R2 = methoxy

In the list above, any of the $R^2$ substituents on compounds 1 through 8 can be any of the $R^2$ substituents labeled a through j. Also, specific compounds are referred to herein by listing the number of the formula above (e.g., 1 through 8) along with the letter of the $R^2$ substituent (e.g., a through j). For example, a compound of formula 1 with $R^2$ as Br (i.e., $R^2$ is the substituent labeled "a") can be referred to as compound "1a."

In the list above, compounds 1-4 are considered sulfonamides and compounds 5-8 are considered sulfones. Among the sulfonamides, compounds 1 and 2 possess a saturated, cyclohexane framework, whereas compounds 3 and 4 possess an unsaturated, cyclohexene framework. Similarly, among the sulfones, compounds 5 and 6 possess a saturated, cyclohexane framework while compounds 7 and 8 possess an unsaturated, cyclohexene framework.

On a cyclic framework containing at least two adjacent substituents, as is shown in Formula I, there can be two chiral centers depending on the substituents. Also, the relative stereochemical orientation of the two substituents can be either cis or trans. Thus, compounds 1, 3, 5, and 7 represent cis isomers while compounds 2, 4, 6, and 8 represent trans isomers. Each of the cis or trans structures represents a racemate consisting of two enantiomers of opposite absolute configurations. For example, the cis-biphenylsulfonamide (1c) represents two cis isomers, one with an αS,βR configuration and the other with an αR,βS configuration. Similarly, the trans-biphenylsulfonamide (2c) represents two trans isomers, one with an αS,βS configuration and the other with an αR,βR configuration. The structures of these particular compounds, 1c and 2c, are shown below.

Other specific examples include, (e.g., compound 3-4c)

(e.g., compound 5-6d)

As described herein, compounds represented by Formula I are modulators of MMPs. While not wishing to be bound by theory, it is believed that since compounds represented by Formula I have hydroxamate groups that can bind Zn, compounds represented by Formula I can be modulators of all Zn-dependent MMPs, for example, MMP-1, MMP-3, MMP-7, MMP-8, MMP-11, and MMP-13, or a mixture thereof. In this respect, compounds represented by Formula I can be said to be broad spectrum MMP modulators.

In another aspect, compounds represented by Formula I are selective modulators of MMPs. In still another aspect, compounds represented by Formula I are selective modulators of MMP-2 and MMP-9. In yet another aspect, compounds represented by Formula I are capable of modulating tumor progression, tumor metastasis, and tumor invasion, and are also antiarthritic agents.

In another aspect, compounds represented by Formula I are potent inhibitors of MMPs. While not wishing to be bound by theory, it is believed that since compounds represented by Formula I have hydroxamate groups that can bind Zn, compounds represented by Formula I can be inhibitors of all Zn-dependent MMPs, for example, MMP-1, MMP-3, MMP-7, MMP-8, MMP-11, and MMP-13, or a mixture thereof. In this respect, compounds represented by Formula I can be said to be broad spectrum MMP inhibitors.

In one aspect, compounds represented by Formula I are selective inhibitors of MMPs. In another aspect, compounds represented by Formula I are selective inhibitors of MMP-2 and MMP-9. In yet another aspect, compounds represented by Formula I are capable of inhibiting tumor progression, tumor metastasis, and tumor invasion, and are also antiarthritic agents.

Synthetic Methods

Compounds represented by Formula I can be readily synthesized using techniques generally known to those of skill in the art. The starting materials and reagents used in preparing these compounds are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4$^{th}$ Edition); and Larock's Comprehensive Organic Transformations (VCH Publishers Inc., 1989).

In one aspect, compounds represented by Formula I can be prepared by methods illustrated in Schemes I and II. These schemes are merely illustrative of some methods by which the compounds disclosed herein can be synthesized, and various modifications to these schemes can be made and will be apparent to one skilled in the art having reviewed this disclosure.

In the following discussion, the starting materials and the intermediates of the reactions can be isolated and purified, if desired, using conventional techniques, including but not limited to, filtration, distillation, crystallization, chromatography, and the like. Such materials can be characterized using conventional means, including physical constants and spectral data. Also, unless specified to the contrary, the reactions described herein can take place at atmospheric pressure over a temperature range from about −78° C. to about 150° C., from about 0° C. to about 125° C., or at about room (or ambient) temperature, e.g., about 20° C.

Scheme I:

Scheme I provides an outline of a synthetic route for accessing the sulfonamide compounds represented by Formula I, wherein Z=NH, e.g., compounds 1, 2, 3, and 4 discussed above, starting with racemic cis- or trans-cyclic amino acid starting material (9). Starting material 9 is commercially available or is synthetically accessible by methods known to those skilled in the art. For example, starting materials cis-2-aminocyclohexanecarboxylic acid (racemic) or trans-2-aminocyclohexanecarboxylid acid (racemic), which lead to compounds 1 and 2, respectively, are available from commercial suppliers such as Acros Organics (Morris Plains, N.J.). Similarly, the use of cyclohexene analogues of 9 as starting materials provide the corresponding cyclohexene compounds 3 and 4. To arrive at individual enantiomers of the final compounds, known chiral, enantiomerically pure cyclic amino acid analogs of 9 can be used as the starting materials. Synthetic procedures for the preparation of enantiomerically pure cyclic amino acids are also known in the art. See N. Harmat, et. al., *Bioorg. Med. Chem. Lett.*, 1998, 8, 1249-1254, which is incorporated by reference herein for its teachings of synthetic procedures for the preparation of enantiomerically pure cyclic amino acids.

In Scheme I, starting material 9 is reacted with a functional derivative of sulfonic acid, R—SO$_2$LG, where LG represents a suitable leaving group, such as, a chloride, anhydride, or mixed anhydride. This reaction can take place under basic conditions suitable to provide the sulfonamide. Suitable bases for this reaction are well known and include, but are not limited to, carbonates, bicarbonates, hydroxides, alkoxides, hydrides, and amines, such as trimethylamine, triethylamine, diisopropylamine, N-ethyl-diisopropyl amine, pyridine, or dimethylaminopyridine, including a mixture thereof. Also, the reaction can be carried out in the presence of an organic solvent, such as dioxane, dichloromethane, 1,2-dichloroethane, 1,1,1-trichloroethane, N,N-dimethylformamide (DMF), N,N-dimethylacetamide, dimethylsulfoxide (DMSO), acetonitrile, ethyl acetate, ether, benzene, toluene, or xylene, including a mixture thereof. In one aspect, the reaction can be carried out with starting material 9 and a sulfonyl chloride (R—SO$_2$Cl) in the presence of sodium carbonate in dioxane-water solvent.

The resulting sulfonamide is subsequently coupled with a protected hydroxylamine, H$_2$N—OPG, where PG represents a protecting group, under suitable amino-acid coupling conditions. Alternatively, the acid function in the sulfonamide is activated, for example, by conversion to the acid chloride or mixed anhydride, and then reacted with a protected hydroxylamine. Protected hydroxyl amines are commercially available or can be prepared by methods known in the art. Typically, protected hydroxylamines are prepared by reacting hydroxylamine with a suitable protecting group. The protecting group that is used will depend on the specific reaction conditions, other substituents that may be present, availability, or preference.

Conditions for coupling the protected hydroxylamine and the sulfonamide are well know in the art and typically involve contacting the sulfonamide with the protected hydroxylamine in the presence of one or more activating agents. Various activating agents that can be used for the coupling reaction include, but are not limited to, 1-ethyl-3-(3-dimethylaminopropyl)carbodiimide (EDC), dicyclohexylcarbodiimide (DCC), N,N'-diisopropyl-carbodiimide (DIP), benzotriazol-1-yl-oxy-tris-(dimethylamino)phosphonium hexa-fluorophosphate (BOP), hydroxybenzotriazole (HOBt), and N-methylmorpholine (NMM), including a mixture thereof. The coupling reaction can be carried out in N-methylpyrrolidone (NMP) or in DMF. In one aspect, the coupling reaction can involve the treatment of the sulfonamide with a protected hydroxylamine in the presence of EDC, HOBt, and NMM in DMF. See Y. Tamura, et al., *J. Med. Chem.*, 1998, 41, 640-649, which is incorporated by reference herein for its teaching of amine-acid coupling reactions.

Conditions for converting acid function to a reactive derivative such as an acid chloride, for example using thionyl chloride or oxalyl chloride, or to an anhydride, for example by reaction with chloroformic esters under appropriate conditions, followed by reaction of these activated intermediates with or without isolation with hydroxylamine or a protected hydroxyl amine are known in the art and can be applied as an alternative method to the coupling of the acid with a protected hydroxylamine. See Y. Tamura, et al., *J. Med. Chem.*, 1998, 41, 640-649.; P. O'Brien, et al., *J. Med. Chem.*, 2000, 43, 156-166; M. Gowravaram, et al., *J. Med. Chem.*, 1995, 38, 2570-2581, which are incorporated herein by reference for their teachings of the preparation and reactions of activated acids.

The final step of Scheme I involves the removal of the protecting group PG under hydrolytic conditions to result in compounds represented by Formula I, wherein Z=NH. Suitable conditions for the removal of the protecting group are discussed later.

Scheme II:

Scheme II provides an outline of a synthetic route for accessing the sulfone compounds represented by Formula I, wherein Z=CH$_2$, e.g., compounds 5, 6, 7, and 8 discussed above, starting with racemic cis- or trans-lactone (10). Scheme II is based on the ring opening reaction of lactones with thiols (R—SH) in the presence of Lewis acid catalysts. Starting material 10 is commercially available or can be synthesized by methods known in the art. To arrive at individual enantiomers of the final compounds, known chiral, enantiomerically pure lactone analogs of 10 can be used as the starting materials. Synthetic procedures for the preparation of enantiomerically pure lactones are also known in the art. See D. Bailey, et al., *J. Org. Chem.*, 1970, 35, 3574-3576; P. Kennewell, et al., *J. Chem. Soc. Perkin. Trans. 1*, 1982, 2563-2570, which are incorporated by reference herein for their teachings of synthetic procedures for the preparation of enantiomerically pure lactones.

The use of appropriate cyclohexane analogs of starting material 10 provide corresponding compounds 5 and 6, whereas the use of appropriate cyclohexene analogs of starting material 10 provide corresponding compounds 7 and 8. The thiol R—SH is commercially available or can be synthesized by methods known in the art.

Lewis acids that are suitable for the ring opening reaction of the lactone 10 are well known in the art. For example, suitable Lewis acids include, but are not limited to, AlC$_3$, AlBr$_3$, SO$_3$ and complexes of SO$_3$, BF$_3$, BF$_3$ etherate, ZnCl$_2$, TiCl$_4$, SbF$_5$, SnCl$_4$ and the like, including a mixture thereof. Suitable solvents include, for example, dichloromethane, 1,2-dichloroethane, 1,1,1-trichloroethane, N,N-dimethylformamide (DMF), N,N-dimethylacetamide, dimethylsulfoxide (DMSO), acetonitrile, ethyl acetate, ether, benzene, toluene, or xylene, including a mixture thereof.

After the lactone is opened, the sulfur is oxidized by methods known in the art. Various oxidizing agents and conditions are discussed in Hudlicky, Oxidations in Organic Chemistry, ACS monograph 186, 1990, which is incorporated by reference herein for its teachings of oxidation reactions. Suitable oxidation agents include, for example, hydrogen peroxide, sodium meta-periodate, oxone (potassium peroxy monosulfate), meta-chloroperoxybenzoic acid, periodic acid and the like, including a mixture thereof. Suitable solvents include, for example, acetic acid (for sodium meta-periodate) and, for other peracids, ethers such as THF and dioxane, and acetonitrile, DMF and the like, including a mixture thereof. For oxone, suitable solvents include, for example, aqueous alcohols, such as methanol, ethanol, and propanol, including a mixture thereof.

Finally, in Scheme II, a protected hydroxylamine ($H_2N$—OPG) is coupled to the sulfone and the protecting group PG removed to result in compounds represented by Formula I. The protected hydroxylamine, as mentioned above, is commercially available or can be prepared by synthetic methods known in the art. Also, the conditions for the coupling reactions are analogous to those coupling conditions discussed above in Scheme I.

The phrase "protecting group" as used herein means a chemical moiety that temporarily modifies a potentially reactive functional group and protects the functional group from undesired chemical transformations. Protecting group chemistry is known to one of skill in the art. See T. Greene, et al., "Protective Groups in Organic Synthesis," $2^{nd}$ ed., Wiley, N.Y., 1991, which is incorporated by reference herein for its teaching of protecting groups and methods of adding and removing protecting groups.

Examples of protecting groups suitable for use with the protected hydroxylamine in either Scheme I or II include, but are not limited to, tertbutyl, benzyl, tetrahydropyranyl, and silyl ethers such as trimethylsilyl, tert-butyldimethylsilyl, and triisopropylsilyl. Hydrolytic and hydrogenolytic conditions for removing protecting groups used herein, which thus reveals the hydroxamate group, are generally well known and will depend on the particular protecting group used. Hydrolytic deprotection can generally be accomplished by hydrolysis under basic conditions or in the presence of a suitable acid, such as hydrochloric acid, hydrobromic acid, acetic acid, trifluoroacetic acid, or by contact with a suitable acidic resin, such as AMBERLYST™ (Rohm Haas, Philadelphia, Pa.) or DOWEX™ (Dow, Midland, Mich.). Suitable solvents include, for example, dichloromethane, 1,2-dichloroethane, 1,1,1-trichloroethane, N,N-dimethylformamide (DMF), N,N-dimethylacetamide, dimethylsulfoxide (DMSO), acetonitrile, ethyl acetate, ether, benzene, toluene, or xylene, including a mixture thereof.

Hydrogenolytic removal of a protecting group such as a benzyl group can be carried out by hydrogenation in the presence of a catalyst such as palladium on carbon at an appropriate temperature and pressure in a suitable solvent.

While the synthetic routes discussed above can be performed as solution-phase multiple parallel syntheses, which involves the synthesis of compounds in individual reaction vessels, other methods can be performed. For example, combinatorial based syntheses or solid phase syntheses can be used and will depend on the particular compounds to be synthesized, the availability of reagents, or preference.

Utility and Administration

The compounds represented by Formula I have many uses. For example, the compounds have uses in areas where modulation or inhibition of MMPs is therapeutically or prophylactically beneficial, such as in treating or preventing cancer and arthritis. In one aspect the compounds represented by Formula I are used to treat a subject with cancer. Such cancer can include, but is not limited to, carcinoma, melanoma, leukemia, or adenoma.

As noted above, MMPs are suitable targets for anticancer agents because Type IV collagenolytic activity is required by metastasizing tumor cells to traverse tissue/vascular membrane barriers. Also, over-production of MMPs clinically correlates with invasive and metastatic behavior of various tumors. Therefore, administering an effective amount of a compound represented by Formula I to modulate or inhibit MMPs, such as MMP-2 and/or MMP-9, can modulate or inhibit such tumor progression events as tumor metastasis, tumor invasion, and angiogenesis.

In one aspect, the compounds represented by Formula I can selectively modulate or inhibit various MMPs. Recently, information regarding the three-dimensional structure of the catalytic domain of several MMPs, e.g., MMP-1, -3, -7, and -8, and of the catalytic domain-inhibitor complexes, determined by X-ray crystallography and NMR-spectroscopy, has become available. See Y. Tamura, et al., *J. Med. Chem.*, 1998, 21, 640-649; R. Kiyama, et al., *J. Med. Chem.*, 1999, 42, 1723-1738; C. J. Burns, et al., *Angew. Chem. Int. Ed.*, 1998, 37, 2848-2850; L. E. Burgess, et al., *Chem. Abst.*, 1998, 128, 127820; A. Pavlovsky, et al., *Protein Sci.*, 1999, 8, 1455-1462; B. Lovejoy, et al., *Science*, 1994, 263, 375-377; T. Stams, et al., *Nature: Struct. Biol.*, 1994, 1, 119-123; W. Bode, et al., *EMBO J.*, 1994, 13, 1263; B. Stockman, et al., *Protein Sci.*, 1998, 7, 2118-2126; 2281-2286. These studies indicate that the core structure of MMPs consists of three alpha helices and five stranded beta sheet and a catalytic zinc ion located at the bottom of the catalytic cleft, coordinated by three histidine ("His") residues. One difference, however, among the various MMPs, is in the shape and size of the S1' pocket, an additional substrate binding domain embedded within the catalyst Zn-binding domain. In contrast to the open S1, S2', and S3' subsites, the S1' pocket penetrates into the core of the MMP enzyme. This S1' pocket is relatively shallow in MMP-1 and MMP-7, and narrow in MMP-9, while being a much deeper channel in MMP-2, MMP-3, and MMP-8.

While not wishing to be bound by theory, it is believed that this unique conformation of the S1' activity domains in MMPs, such as MMP-2 and MMP-9, contributes to the specificity of the disclosed compound. Compounds represented by Formula I, which incorporate conformational restraint at the α- and β-position of the hydroxamate group with a sulfonyl substituent extending from the exocyclic γ-position, can selectively occupy the deep S1' pocket of the active sites of MMP-2 and MMP-9. Also, while not wishing to be bound by theory, it is believed that the conformationally restrained framework present in compounds represented by Formula I aids in the projection of the sulfonyl substituent toward the S1' pocket, whereas lack of conformational restraint is believed to lead to inhibitors lacking potency due to greatly increased conformational flexibility.

In one aspect, a method for using compounds represented by Formula I comprises administering an amount effective for modulation of a MMP of at least one compound represented by Formula I to an environment comprising the MMP. The MMP can be any MMP or mixtures of MMPs. In one aspect, the MMP is MMP-2, MMP-9, or a mixture thereof.

In another aspect, a method for using compounds represented by Formula I comprises administering an amount effective for inhibition of a MMP of at least one compound represented by Formula I to an environment comprising the MMP. The MMP can be any MMP or mixtures of MMPs. In one aspect, the MMP is MMP-2, MMP-9, or a mixture thereof.

In yet another aspect, an amount effective for modulation of a MMP of at least one compound represented by Formula I is administered to an environment comprising the MMP. In still another aspect, an amount effective for inhibition of a MMP of at least one compound represented by Formula I is administered to an environment comprising the MMP. Again, the MMP can be any MMP, e.g., MMP-2, MMP-9, or mixtures of MMPs. In one aspect, the compound represented by Formula I that is administered to an environment comprising a MMP is compound 1c, 2c, or a mixture thereof.

The administration of compounds represented by Formula I to an environment comprising a MMP can be conducted in vivo or in vitro.

In one aspect, a method for using a compound represented by Formula I comprises administering an amount effective for modulation of tumor metastasis of at least one compound represented by Formula I to a subject or cell. In another aspect, a method for using a compound represented by Formula I comprises administering an amount effective for inhibition of tumor metastasis of at least one compound represented by Formula I to a subject or cell. In still another aspect, the cell is a HT-1080 cell.

In one aspect, the amount effective for modulation is equivalent to an amount effective for inhibition. Modulation and/or inhibition of the MMP can be measured by methods known in the art. In one aspect, modulation can be measured by any change in tumor invasion and inhibition can be measured by arrest of tumor invasion. In another aspect, modulation can be measured by any change in tumor angiogenesis and inhibition can be measured by arrest of tumor angiogenesis. Inhibition potency can be characterized by an $IC_{50}$ less than about 3000 nM, less than about 1500 nM, less than about 1000 nM, less than about 500 nM, or less than about 200 nM.

In one aspect, the compounds described herein can be administered to a subject in need of treatment, such as a subject with cancer or arthritis. The subject in need of treatment can comprise a human or an animal including, but not limited to, a rodent, dog, cat, horse, bovine, ovine, or non-human primate and the like, that is in need of alleviation or amelioration from a recognized medical condition.

Any of the compounds represented by Formula I can be delivered to a subject as part of a cocktail, i.e., used in combination with other pharmaceutical agents. For example, the compounds represented by Formula I can be part of an anti-cancer cocktail, i.e., one or more of the compounds represented by Formula I an be used with one or more anti-cancer agents. The use of cocktails in the treatment of cancer is routine. In one aspect, an anti-cancer cocktail involves a common administration vehicle (e.g., pill, tablet, implant, injectable solution, etc.) that can contain effective amounts of both one or more compounds represented by Formula I and one or more an anti-cancer drugs. Alternatively, an anti-cancer cocktail involves the sequential, simultaneous, or scheduled administration of effective amounts of one or more compounds represented by Formula I and one or more anti-cancer drugs. For example, one or more compounds represented by Formula I can first be given to a subject and then, after some period of time, an anti-cancer agent is given to the subject. The order of administration can be determined by one skilled in the art depending on factors such as the particular type of anti-cancer drug, the type and severity of the cancer, and the like.

Suitable anti-cancer agents that can be used in an anti-cancer cocktail with the compounds represented by Formula I include, but are not limited to, Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemeitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

Modulators or inhibitors of MMPs can provide synergistic effects when used in a cocktail. For example, the use of other MMP modulators or inhibitors in combination with anti-cancer agents has been known to produce synergistic effects, i.e., the amount of modulation or inhibition observed when using a combination of MMP modulator or inhibitor and anti-cancer agent is greater than the amount of modulation or inhibition observed when either is used alone. See M. Ohta et al., *Japanese J. Cancer. Res.*, 2001, 92, 688; M. Maki et al., *Clin. Exp. Metastasis*, 2002, 19, 519. Accordingly, the use of compounds represented by Formula I can provide synergistic effects when administered as part of an anti-cancer cocktail.

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject in need of attention for the treatment of cancer, arthritis, or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: 1) a subject's physical condition is shown to be improved (e.g., a tumor has partially or fully regressed), 2) the progression of the disease or condition is shown to be stabilized, or slowed, or reversed, or 3) the need for other medications for treating the disease or condition is lessened or obviated, then a particular treatment regimen will be considered efficacious.

Any of the compounds represented by Formula I can be used therapeutically in combination with a pharmaceutically acceptable carrier. In another aspect, any of the compounds represented by Formula I can be used prophylactically, i.e., as a preventative agent, with a pharmaceutically acceptable carrier. The compounds described herein can be conveniently formulated into pharmaceutical compositions composed of one or more of the compounds in association with a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. Such pharmaceutical carriers, most typically, would be standard carriers for administration of compositions to humans and non-humans, including solutions such as sterile water, saline, and buffered solutions at physiological pH. Other compounds will be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more additional active ingredients such as antimicrobial agents, antiinflammatory agents, anesthetics, and the like.

The compounds and pharmaceutical compositions, described herein can be administered to the subject in a number of ways depending on whether local or systemic treatment is desired, and on the area to be treated. Thus, for example, a compound or pharmaceutical composition described herein can be administered as an ophthalmic solution and/or ointment to the surface of the eye. Moreover, a compound or pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein for its teaching of sustained release systems.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives, such as antimicrobials, anti-oxidants, chelating agents, and inert gases and the like, can also be present.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

(cis)-2-[[(4-Biphenyl)sulfonyl]amino]cyclohexanecarboxylic acid: A stirred solution of cis-2-amino-1-cyclohexanecarboxylic acid (2.4 g, 16.76 mmol) and sodium carbonate (3.553 g, 33.52 mmol) in dioxane:water (168:84 mL) was cooled in ice-water bath and to the cold solution was added biphenyl-4-sulfonyl chloride (4.85 g, 19.15 mmol) in one portion. The reaction mixture was stirred in the cold bath for 2 hours. After allowing the reaction mixture to attain room temperature, the mixture was stirred for an additional 48 hours. The mixture was then poured into 10% aqueous citric acid (500 mL) and the mixture was stirred for 2 hours. The solid obtained was collected by filtration. The solid was stirred with 1N aqueous sodium hydroxide and the solution was filtered to remove any insoluble material. The alkaline aqueous filtrate was cooled and acidified to pH 1 with concentrated aqueous hydrochloric acid. The solid obtained was collected by filtration, washed with water and dried in air to obtain the desired acid as a colorless solid. The procedure yielded 3.78 g (63%) of (cis)-2-[[(4-Biphenyl)sulfonyl]amino]cyclohexanecarboxylic acid, which had a melting point of 188-190° C. Mass spectrometry revealed molecular ion peak (MH)$^+$ at m/z 360. Proton NMR analysis in CDCl$_3$ resulted in the following chemical shifts ($\delta$): 1.2-2.1 (m, 8H, cyclohexyl methylenes), 2.70-2.85 (m, 1H, C-1H), 3.40-3.55 (m, 1H, C-2H), 5.95 (d, 1H, SO$_2$NH), 7.35-8.0 (m, 9H, biphenyl-H), 8.75 (broad s, 1H, CONH), and 10.45 (broad s, 1H, N—OH), where s is a singlet, d is a doublet, m is a multiplet.

Example 2

(cis)-N-Hydroxy-2-[[(4-Biphenyl)sulfonyl]amino]cyclohexanecarboxamide (compound 1c): A solution of the acid obtained in Example 1 (0.80 g, 2.23 mmol) in CH$_2$Cl$_2$ (30 mL) was cooled in an ice bath and treated with oxalyl chloride (1.415 g, 11.15 mmol) followed by one drop of N,N-dimethylformamide as a catalyst. The reaction mixture was then allowed to warm to room temperature and stir at room temperature for 2 hours. Volatile material from the reaction mixture was then removed under reduced pressure, and the residue was dried under high vacuum for an hour. The acid chloride thus obtained was dissolved in anhydrous tetrahydrofuran (10 mL), cooled to 0° C., and treated dropwise with O-(trimethylsilyl)hydroxylamine (2.35 g, 22.3 mmol). The mixture was allowed to attain room temperature and stir overnight. The reaction mixture was concentrated under reduced pressure and the residue was dissolved in ethyl acetate (200 mL). The solution was successively washed with 1 N hydrochloric acid (100 mL) and brine (100 mL). The organic layer was dried with anhydrous sodium sulfate, filtered, and the solvent was removed under reduced pressure. The solid thus obtained was recrystallized from ethyl acetate/hexane to yield 0.63 g (75%) of the desired product 1c. The product 1c had a melting point of 74-76° C. Mass spectrometry revealed a molecular ion peak (MH)$^+$ at m/z 375. Proton NMR analysis in DMSO-d$_6$ resulted in the following chemical shifts ($\delta$): 1.0-2.1 (m, 8H, cyclohexyl methylenes), 2.30-2.40 (m, 1H, C-1H), 3.20-3.35 (m, 1H, C-2H), 7.35-8.00 (m, 10H, biphenyl-H and SO$_2$NH), 8.75 (broad s, 1H, CONH), and 10.45 (broad s, 1H, N—OH).

Example 3

(trans)-2-[[(4-Biphenyl)sulfonyl]amino]cyclohexanecarboxylic acid: This compound was prepared from trans-2-amino-1-cyclohexanecarboxylic acid (1.0 g, 7.0 mmol) by reacting it with sodium carbonate (1.48 g, 14.0 mmol) and biphenyl-4-sulfonyl chloride (2.02 g, 8.0 mmol) in dioxane: water (70:35 mL) in the same manner as described in Example 1. The yield was 1.48 g (59%), the melting point was 220-222° C., and mass spectrometry revealed a molecular ion peak (MH)$^+$ at m/z 360.

Example 4

(trans)-N-Hydroxy-2-[[(4-Biphenyl)sulfonyl]amino]cyclohexanecarbox-amide (compound 2c): A solution of the acid obtained in Example 3 (0.56 g, 1.56 mmol) was reacted with oxalyl chloride (0.99 g, 7.8 mmol) followed by O-(trimethylsilyl)-hydroxylamine (1.64 g, 15.6 mmol) as described in Example 2 to obtain 0.23 g (40%) of 2c. The melting point was 212-214° C. Mass spectrometry revealed a molecular ion peak (MH)$^+$ at m/z 375. Proton NMR analysis in DMSO-d$_6$ resulted in the following chemical shifts ($\delta$): 0.90-1.85 (m, 8H, cyclohexyl methylenes), 1.90-2.05 (m, 1H, C-1 H), 3.25-3.45 (m, 1H, C-2H), 7.40-7.90 (m, 10H, biphenyl-H and SO$_2$NH), 8.75 (broad s, 1H, CONH), and 10.24 (broad s, 1H, N—OH).

Example 5

(cis)-2-[(4-Phenoxybenzenesulfonyl)amino]cyclohexanecarboxylic acid: This compound was prepared from cis-2-amino-1-cyclohexanecarboxylic acid (1.0 g, 7.0 mmol) by reacting it with sodium carbonate (1.48 g, 14.0 mmol) and 4-phenoxybenzenesulfonyl chloride (2.25 g, 8.38 mmol) in dioxane:water (40:20 mL) in the same manner as described in Example 1. This yielded 2.23 g (85%). The melting point was 116-118° C. Mass spectrometry revealed a molecular ion peak (MH)$^+$ at m/z 376. Proton NMR analysis in CDCl$_3$ resulted in the following chemical shifts ($\delta$): 1.2-2.2 (m, 8H, cyclohexyl methylenes), 2.75-2.85 (m, 1H, C-1H), 3.62-3.50 (m, 1H, C-2 H), 5.92 (d, 1H, SO$_2$NH), and 6.99-7.86 (m, 9H, aryl-H).

Example 6

(cis)-N-Hydroxy-2-[(4-Phenoxybenzenesulfonyl)amino]cyclohexanecarbox-amide (compound 1d): A solution of the acid obtained in Example 5 (0.56 g, 1.49 mmol) was reacted with oxalyl chloride (2M solution in CH$_2$Cl$_2$, 3.7 mL, 7.4 mmol) followed by O-(trimethylsilyl)hydroxylamine (1.56 g, 14.91 mmol) as described in Example 2 to obtain 0.275 g (48%) of the desired product. The melting point was 66-68° C. Mass spectrometry revealed a molecular ion peak (MH)$^+$ at m/z 391. Proton NMR analysis in DMSO-d$_6$ resulted in the following chemical shifts ($\delta$): 1.06-1.94 (m, 8H, cyclohexyl methylenes), 2.29-2.36 (m, 1H, C-1H), 3.19-3.28 (m, 1H, C-2H), 7.08-7.86 (m, 10H, biphenyl-H and SO$_2$NH), 8.8 (broad s, 1H, CONH), and 10.4 (broad s, 1H, N—OH).

Example 7

(trans)-2-[(4-Phenoxybenzenesulfonyl)amino]cyclohexanecarboxylic acid: This compound was prepared from trans-2-amino-1-cyclohexanecarboxylic acid (1.0 g, 7.0 mmol) by reacting it with sodium carbonate (1.48 g, 14.0 mmol) and 4-phenoxybenzenesulfonyl chloride (2.25 g, 8.38 mmol) in dioxane:water (40:20 mL) in the same manner as described in Example 1. This yielded 1.275 g (48%). The melting point was 192-194° C. Mass spectrometry revealed a molecular ion (MH)$^+$ peak at m/z 376.

Example 8

(trans)-N-Hydroxy-2-[(4-Phenoxybenzenesulfonyl)amino]cyclohexane-carboxamide (compound 2d): A solution of the acid obtained in Example 7 (1.00 g, 2.66 mmol) was reacted with oxalyl chloride (2M solution in $CH_2Cl_2$, 6.65 mL, 13.3 mmol) followed by O-(trimethylsilyl)hydroxylamine (2.8 g, 26.64 mmol) as described in Example 2 to obtain 0.48 g (46%) of the desired product. The melting point was 182-184° C. Mass spectrometry revealed a molecular ion (MH)$^+$ peak at m/z 391. Proton NMR analysis in $CDCl_3$ resulted in the following chemical shifts ($\delta$): 0.98-1.96 (m, 8H, cyclohexyl methylenes), 2.05-2.16 (m, 1H, C-1H), 3.50-3.67 (broad hump, 1H, C-2H), 6.15 (broad hump, 1H, $SO_2NH$), 7.01-7.88 (m, 9H, aryl-H), and 8.98 (broad s, 1H, CONH).

Example 9

(cis)-2-[[(4-Phenylazo)benzenesulfonyl]amino]cyclohexanecarboxylic acid: This compound was prepared from cis-2-amino-1-cyclohexanecarboxylic acid (1.0 g, 7.0 mmol) by reacting it with sodium carbonate (1.48 g, 14.0 mmol) and 4-(phenylazo)benzenesulfonyl chloride (2.35 g, 8.38 mmol) in dioxane:water (40:20 mL) in the same manner as described in Example 1. This yielded 0.915 g (33%). Mass spectrometry revealed a molecular ion peak (MH)$^+$ at m/z 388. Proton NMR analysis in $CDCl_3$ resulted in the following chemical shifts ($\delta$): 1.2-1.9 (m, 8H, cyclohexyl methylenes), 1.98-2.14 (m, 1H, C-1H), 3.45-3.60 (m, 1H, C-2H), 5.9 (broad hump, 1H, $SO_2NH$), and 7.50-8.05 (m, 9H, aryl-H).

Example 10

(cis)-N-Hydroxy-2-[[(4-Phenylazo)benzenesulfonyl]amino]cyclohexane-carboxamide (compound 1g): A solution of the acid obtained in Example 9 (0.915 g, 2.36 mmol) was reacted with oxalyl chloride (2M solution in $CH_2Cl_2$, 5.91 mL, 11.82 mmol) followed by O-(trimethylsilyl)hydroxylamine (2.48 g, 23.64 mmol) as described in Example 2 to obtain 0.44 g (46%) of the desired product. The melting point was 162-164° C. Mass spectrometry revealed a molecular ion peak (MH)$^+$ at m/z 403. Proton NMR analysis in $CDCl_3$ resulted in the following chemical shifts ($\delta$): 0.71-2.05 (m, 8H, cyclohexyl methylenes), 2.6-2.7 (m, 1H, C-1H), 2.30-2.41 (m, 1H, C-2H), 6.1-6.2 (broad hump, $SO_2NH$), 7.5-8.1 (m, 10H, aryl-H), and 8.3-8.6 (broad hump, 2H, CONH, N—OH).

Example 11

(trans)-2-[[(4-Phenylazo)benzenesulfonyl]amino]cyclohexanecarboxylic acid. This compound was prepared from trans-2-amino-1-cyclohexanecarboxylic acid (1.0 g, 7.0 mmol) by reacting it with sodium carbonate (1.48 g, 14.0 mmol) and 4-(phenylazo)benzenesulfonyl chloride (2.35 g, 8.38 mmol) in dioxane:water (40:20 mL) in the same manner as described in Example 1. This yielded 1.02 g (37%). The melting point was 246-248° C. Mass spectrometry revealed a molecular ion peak at (MH)$^+$ m/z 388. Proton NMR analysis in $CDCl_3$ resulted in the following chemical shifts ($\delta$): 1.0-1.98 (m, 8H, cyclohexyl methylenes), 2.05-2.14 (m, 1H, C-1H), 3.35-3.45 (m, 1H, C-2 H), 4.88-4.99 (broad hump, 1H, $SO_2NH$), and 7.5-8.1 (m, 9H, aryl-H).

Example 12

(trans)-N-Hydroxy-2-[[(4-Phenylazo)benzenesulfonyl]amino]cyclohexane-carboxamide (compound 2g): A solution of the acid obtained in Example 11 (1.00 g, 2.58 mmol) was reacted with oxalyl chloride (2M solution in $CH_2Cl_2$, 6.45 mL, 12.9 mmol) followed by O-(trimethylsilyl)hydroxylamine (2.72 g, 25.84 mmol) as described in Example 2 to obtain 0.35 g (33%) of the desired product. The melting point was 194-196° C. Mass spectrometry revealed a molecular ion peak (MH)$^+$ at m/z 403. Proton NMR analysis in $CDCl_3$ resulted in the following chemical shifts ($\delta$): 0.98-1.98 (m, 8H, cyclohexyl methylenes), 2.10-2.22 (m, 1H, C-1H), 3.60-3.78 (m, 1H, C-2H), 6.35 (d, 1H, $SO_2NH$), 7.50-8.15 (m, 9H, aryl-H), and 8.9-9.0 (broad hump, 2H, CONH, N—OH).

Example 13

Enzyme Inhibition Assays: The enzyme inhibition kinetics ($IC_{50}$) of nonpeptidyl compounds 1c and 2c were determined using purified MMP-2, MMP-3, and MMP-9 using standard fluorometric substrate-degradation assays. Human rMMP-2 and -9 were purified in active forms, and purified MMP-1, -3 and -13 were obtained from commercial sources (Chemicon; Temecula, Calif.) in zymogen form and were activated by 1 mM APMA or PCMB treatment (2 hrs at 37° C.). For kinetic studies, a standard fluorimetric assay based on hydrolysis of fluorogenic synthetic substrate (1 µM of McaPLGLDpaAR) was used. For each assay, target MMP (1 µM) and increasing concentrations of test compound were incubated at 25° C. for 30-60 min and the rate of substrate hydrolysis was measured by Perkin-Elmer fluorometer at an excitation 328 nm and an emission 393 nm settings. Both concentration and time-dependent cleavage were monitored. Controls included trypsin (non-specific cleavage) and bacterial collagenase (total cleavage) and other zinc-protease (ACE, endopeptidase). $IC_{50}$ values (the concentration at which 50% enzyme activity is inhibited) were determined by plots of % activity versus negative log of agent concentration. The $IC_{50}$ values were converted to $K_i$ values using the equation, $K_i=IC_{50}/(1+S/K_m)$. The $K_m$ values (µM) were calculated from the $K_i$ values of 3-5 separate experiments. Inhibition kinetics of various MMPs were also determined using substrate-degradation ELISA kits from Chemicon (Temecula, Calif.). See C. Knight, et al., *FEBS Lett.*, 1992, 296, 263-266; L. Windsor, et al., *Biochem. Biophys. Acta* 1977, 1334, 261-272, which are incorporated by reference herein for their teachings of enzyme inhibition assays.

MMP inhibitor selectivity determinations: Both quantitative labeled-substrate and FITC-biopeptide (matrix-specific) assays were used to examine the selective inhibition of MMP activities. Substrate specificity for MMP-1, -2, and -9 was assessed by degradation of labeled-collagen I and IV. Typically, MMP-dependent biomatrix degradation was monitored in the presence and absence of candidate compounds (0.5-500 µm) after 60-90 min incubations. Inhibitory potency and selectivity was also analyzed using a gelatin or collagen zymography followed by densitometric analysis. Labeled collagen I or IV degradation assay (zymography) was used for M-1, -2 and -9 activities and their inhibition. Bacterial collagenase and EDTA (10 mM) was included as positive and negative controls. In situ zymography film technique was also used for measurement of MMP-2 and MMP-9 (gelatinolytic) activities and their inhibition by drug treatment in target cells and tissue samples. For evaluation of MMP selectivity, two human HT-1080 cancer cell sublines, which produce in abundance different levels of MMP-2 and MMP-9 were used. The HT-1080-B subline produces predominantly MMP-9 (2 mg/L) while HT-1080-R cells are abundant in MMP-2 (1 mg/L). Both cell lines also secrete small amounts of other MMPs including MMP-1 and MMP-3 (<1%). See G. Siegal, et al., *Cancer Lett.* 1993, 69, 123-132; L. Goodly, et al., Tumor Biology 1994, 15, 326-336; M. Ikeda, et al., *Clin. Cancer. Res.* 2000, 6, 3290-3296.

The results presented in Table 1 demonstrate that both sulfonamide compounds selectively inhibit MMP-2 and MMP-9 activities, over MMP-3 and endopeptidase. These inhibition profiles were compared with a potent broad range MMP inhibitor GM-6001, which is available from Chemicon (Temecula, Calif.). Negative controls included other proteases, e.g., trypsin or amidopeptidase, whose activities were unaffected (up to 0.1 mM).

TABLE 1

Inhibition Potencies of Nonpeptidyl Compounds Against Selected Enzymes.

| Compound | Inhibition Potencies, $IC_{50}$ (nM) | | | |
|---|---|---|---|---|
| | MMP-2 | MMP-9 | MMP-3[a] | Endopeptidase |
| 2c | 125 | 145 | >3000 | >20000 |
| 1c | 150 | 175 | >3000 | >20000 |
| GM-6001 | 2 | 2 | 80 | not detectable |

[a]Minienzyme used.

Example 14

Tumor Invasion and Angiogenesis Assays: The multi-step metastatic cascade involves MMP-mediated tissue matrix degredation, angiogenesis, tumor cell migration/invasion and subsequent colonization at distant sites (M. Crocket, et al., *Biochem Soc. Symp.*, 1998, 63, 295-313; D. Keiner, et al., *Metastasis Rev.*, 1990, 9, 289-303; J. MacDougall, et al., *Mol. Med. Today*, 2000, 64, 149-56). These functional events have been mostly studied using biomatrix co-culture systems such as collagen gels and MATRIGEL™ (available from Becton-Dickinson, Bedford, Mass.; see R. Auerbach, et al., *Pharm. Ther.*, 1991, 51, 1-11; H. Kleinman, et al., *Biochem.*, 1986, 25, 312-318). However, these models exhibit compositional complexity and biological limitations. For example, the mouse tumor derived MATRIGEL™ contains major mitogenic and differentiation factors as well as proteases which may trigger undefined cell-matrix interactions (S. Vulicevik, et al., *Exp. Cell Res.*, 1992, 202, 1-8). To overcome these difficulties a new human biomatrix, Amgel, which is free of collagenases and mitogenic factors, was used for examining the functional behavior of target cells (G. Siegel, et al., *Cancer Lett.*, 1993, 69, 123-132).

The hallmarks of the Amgel system are that it mimics a physiological matrix barrier, and Amgel alone is neither angiogenic nor tumorigenic, but exhibits controlled bioactivity both in vitro and in vivo. Also, the Amgel bioassay can identify single modulators (natural and synthetic agents) of human cell invasion, motility and angiogenesis. Moreover, the Amgel biomatrix contains both human collagen I and IV, the in vivo footprints of MMP-1 activity and MMP-2 and -9 activities, respectively. Thus, Amgel bioassays are useful for identifying the selectivity of MMP inhibitors while discriminating their effects on different stages of tumorigenesis. Accordingly, to validate if MMP inhibition translated into a biological effect, Amgel human tumor invasion and angiogenesis models were employed.

Human tumor cell invasion bioassay: Amgel-coated filters (8 μm) were used as tissue biomatrix barriers placed between Lucite chambers. Labeled cells (50,000) were seeded onto reconstituted-Amgel filters (75 μg) and the lower chambers were filled with media containing 5% dialyzed serum. Test compounds (0.5-100 μM) were added and incubated for 72 hours. Contents from the lower chamber were collected to resolve cell-bound and free radioactivity. See G. Siegal, et al., *Cancer Lett.* 1993, 69, 123-132; L. Goodly, et al., *Tumor Biology* 1994, 15, 326-336; M. Ikeda, et al., *Clin. Cancer. Res.* 2000, 6, 3290-3296; R. Singh, et al., *In Vitro Cell Develop. Biol.*, 2002, 38, 11.

Human tumor angiogenesis bioassay: Angiogenesis was induced by coculture of human endothelial cells (HUVECs) with tumor cells or defined angiogenic factor (FGF). Tumor cells media (from 24-hour serum-free cultures) were used to induce a biological angiogenic response using human glioma cell lines producing different concentrations of VEGF or by using purified factors such as 20 μM FGF. Endothelial cells were seeded onto Amgel-coated filters and induced with a angiogenic media+/−candidate MMP inhibitors. Varying concentrations of test compounds (0.5-500 μM) and incubation times (1-7 days) were applied, and endothelial cell differentiation (sprouting and tubule-like capillary formation) were examined by light microscopy and a computerized digital system.

Figure 1:
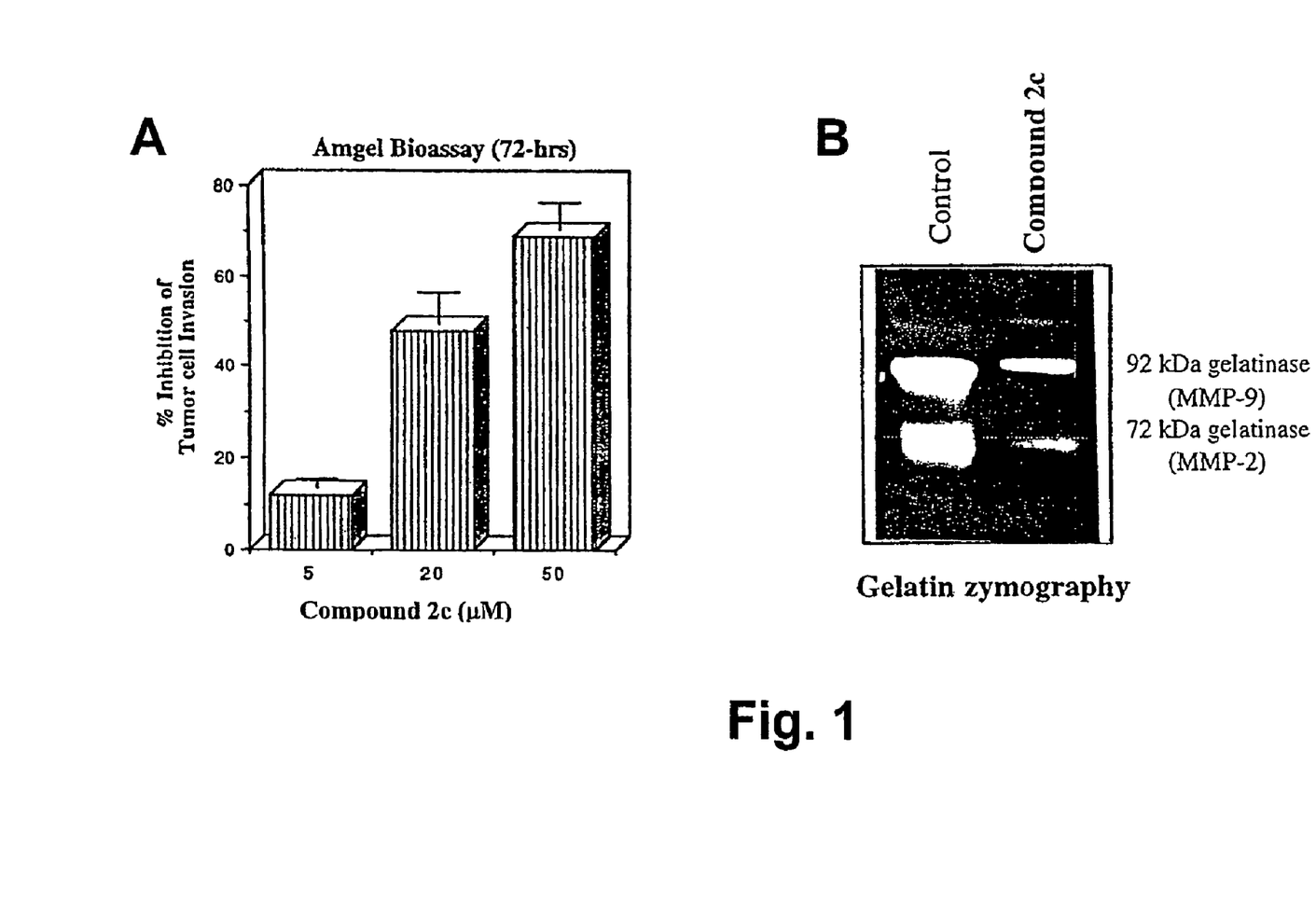
FIG. 1A is a graph showing % inhibition of tumor invasion for various concentrations of compound 2c in the Amgel tumor invasion bioassay.
FIG. 1B is a gelatin zymograph showing MMP-2 and MMP-9 activity inhibition with compound 2c.

Evaluation of the compounds 1c and 2c in Amgel human tumor invasion and angiogenesis models (72 hours incubation at 50-100 μM) was performed using two human HT-1080 cancer cell sublines (HT-1080-B and HT-1080-R). The results of these assays with compound 2c are shown in Table 2 and FIG. 1 (data for compound 1 c not shown).

TABLE 2

Inhibition Potencies of Compound 2c in Cell-Function Assays.

| | % Inhibition | |
|---|---|---|
| Cell line | Tumor invasion | Tumor angiogenesis |
| HT-1080R | 60 ± 5 | 40 ± 6 |
| HT-1080B | 50 ± 8 | 45 ± 4 |
| HF | No effect | No effect |

Functional evaluation of compounds 1c and 2c revealed a marked (40-60%) reduction in the invasiveness and angiogenesis of highly tumorigenic human HT-1080 cell lines. Also, neither compound 1c nor compound 2c had any effect on nontumorigenic human fibroblasts cells (HF). Further, compounds 1c and 2c were observed to have no effect on the cell proliferation and cell viability at the tested concentrations (data not shown).

The arrest of tumor invasion by compounds 1c and 2c paralleled their profiles in inhibiting MMP-2 and MMP-9 activities, as measured by degree of gelatin degradation by electrophoresed cell media. The inhibition potencies of the compounds in the parental HT-1080 cells producing both MMP-2 and MMP-9 were much higher (>70%) than their inhibition potencies in cell lines producing a single form of MMP. These observations indicate that compounds 1c and 2c produce synergistic effects through simultaneous inhibition of MMP-2 and MMP-9.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A compound having the following formula:

wherein

X is $(CH_2)_n(CH_2)$, or $CH=CH$, wherein n=0, 1, or 2;
R is a substituted aryl group of the following formula:

$R^2$ is Br; methoxy;

wherein Y=O, S, or $CH_2$;

Z is NH or $CH_2$;
or a pharmaceutically acceptable salt thereof.

2. The compound of claim 1, wherein Z is NH.
3. The compound of claim 1, wherein Z is $CH_2$.
4. The compound of claim 1, wherein R is:

5. The compound of claim 1, wherein X is $(CH_2)_n(CH_2)$ and n=1.
6. The compound of claim 1, wherein X is $CH=CH$.

7. The compound of claim 1, wherein the compound is or a pharmaceutically acceptable salt thereof.

8. The compound of claim 1, wherein the compound is or a pharmaceutically acceptable salt thereof.

9. The compound of claim 1, wherein the compound is or a pharmaceutically acceptable salt thereof.

10. The compound of claim 1, wherein the compound is or a pharmaceutically acceptable salt thereof.

11. The compound of claim 1, wherein the compound is or a pharmaceutically acceptable salt thereof.

12. A pharmaceutical composition, comprising a compound having the following formula:

wherein
X is $(CH_2)_n(CH_2)$ or $CH=CH$, wherein n=0, 1, or 2;
R is a substituted aryl group of the following formula:

$R^2$ is Br; methoxy;

wherein Y=O, S, or $CH_2$;

Z is NH or $CH_2$;
or a pharmaceutically acceptable salt thereof,
and a pharmaceutical carrier.

13. The composition of claim 12, wherein the compound is or a pharmaceutically acceptable salt thereof.

14. The composition of claim 12, wherein the compound is or a pharmaceutically acceptable salt thereof.

* * * * *